(12) United States Patent
Kwon

(10) Patent No.: US 9,057,929 B2
(45) Date of Patent: Jun. 16, 2015

(54) QUINOLINIUM SINGLE CRYSTALS FOR USE IN NONLINEAR OPTICS

(71) Applicant: AJOU UNIVERSITY INDUSTRY-ACADEMIC COOPERATION FOUNDATION, Suwon-si (KR)

(72) Inventor: O-Pil Kwon, Suwon-si (KR)

(73) Assignee: AJOU UNIVERSITY INDUSTRY-ACADEMIC COOPERATION FOUNDATION, Suwon-si (KR)

(*) Notice: Subject to any disclaimer, the term of this patent is extended or adjusted under 35 U.S.C. 154(b) by 0 days.

(21) Appl. No.: 14/193,471

(22) Filed: Feb. 28, 2014

(65) Prior Publication Data

US 2014/0204457 A1 Jul. 24, 2014

Related U.S. Application Data

(63) Continuation of application No. PCT/KR2012/006991, filed on Aug. 31, 2012.

(30) Foreign Application Priority Data

Aug. 31, 2011 (KR) .................. 10-2011-0087771

(51) Int. Cl.
| | |
|---|---|
| G02F 1/355 | (2006.01) |
| C07C 309/30 | (2006.01) |
| C07C 309/35 | (2006.01) |
| C07C 309/42 | (2006.01) |
| C07C 309/43 | (2006.01) |
| C07C 215/14 | (2006.01) |
| G02F 1/35 | (2006.01) |
| G02F 1/361 | (2006.01) |

(52) U.S. Cl.
CPC ............ *G02F 1/3551* (2013.01); *C07C 309/30* (2013.01); *C07C 309/35* (2013.01); *C07C 309/42* (2013.01); *C07C 309/43* (2013.01); *C07C 215/14* (2013.01); *G02F 1/3534* (2013.01); *G02F 1/3612* (2013.01); *G02F 2203/13* (2013.01)

(58) Field of Classification Search
CPC ... G02F 1/3534; G02F 1/3551; G02F 1/3612; G02F 2203/13
USPC ................. 359/326–332; 372/21–22; 546/179
See application file for complete search history.

(56) References Cited

U.S. PATENT DOCUMENTS

| | | | | |
|---|---|---|---|---|
| 4,939,388 A | * | 7/1990 | Eaton et al. .................... | 359/328 |
| 5,101,411 A | * | 3/1992 | Terao et al. ...................... | 372/21 |
| 5,290,485 A | * | 3/1994 | Gotoh et al. ................... | 252/589 |
| 5,346,653 A | * | 9/1994 | Ozaki et al. .................... | 252/582 |

FOREIGN PATENT DOCUMENTS

| | | | | | |
|---|---|---|---|---|---|
| FR | 2681321 A1 | * | 3/1993 | ........... | C07D 213/30 |
| JP | 03284734 A | * | 12/1991 | ................ | G02F 1/35 |

* cited by examiner

*Primary Examiner* — Daniel Petkovsek
(74) *Attorney, Agent, or Firm* — NSIP Law

(57) ABSTRACT

The present invention relates to quinolinium-derived single crystals for use in nonlinear optics, which exhibit high molecular orientation and macroscopic optical nonlinearity. When the quinolinium-derived crystals according to the present invention are applied to THz wave light sources, higher THz wave generating efficiency may be obtained as compared with inorganic crystals or existing organic crystals.

4 Claims, 12 Drawing Sheets
(12 of 12 Drawing Sheet(s) Filed in Color)

(a)

(b)

(a)

(b)

(c)

(a)

(b)

QUINOLINIUM SINGLE CRYSTALS FOR USE IN NONLINEAR OPTICS

CROSS-REFERENCE TO RELATED APPLICATION(S)

This application is a Bypass-Continuation Application of PCT Application No. PCT/KR2012/006991, filed on Aug. 31, 2012, which claims priority to Korean Patent Application No. 10-2011-0087771, filed on Aug. 31, 2011, in the Korean Intellectual Property Office, the entire disclosures of which is incorporated herein by reference for all purposes.

TECHNICAL FIELD

The present invention relates to quinolinium derivative single crystals for use in nonlinear optics (or electro-optics) so as for terahertz wave applications, and particularly to a quinolinium derivative for use in nonlinear optics with high orientation and large macroscopic optical nonlinearity.

BACKGROUND ART

A terahertz (THz) wave indicates an electromagnetic wave having unique properties in the range of 0.3~30 THz, which shows sensitivity for the optical phonon mode related with molecular rotation and vibration, high absorbability for semiconductor and conductor materials, low absorbability for non-conductive materials, and harmlessness for biological systems. Accordingly, THz wave application fields such as THz image systems and THz time-domain spectroscopy based on such a THz wave having unique properties are regarded as more and more important.

However, a THz wave generation source (light source) reported to date exhibits low efficiency and narrow bandwidth, and thus THz wave application techniques are limited.

The most important aim of the THz wave techniques is to develop a THz generation source having a wide bandwidth and high efficiency.

Electro-optic crystals are a promising material for generating a wide THz wave by use of a method such as optical rectification (OR) or difference frequency generation (DFG).

Currently useful inorganic crystals such as ZnTe and GaAs are THz light sources widely employed for these techniques.

Recently, by using organic electro-optic crystals, great improvements in THz generation and detection have been made. Organic crystals having the greatest performance based on dimethylamino-stilbazolium and non-ionic configurationally locked polyene (CLP) groups show large macroscopic nonlinearity with a maximum electro-optic coefficient of $r_{iii}$=53 pm/v at 1.3 μm, whereas inorganic ZnTe crystals show $r_{41}$=4.1 pm/v.

So large macroscopic nonlinearity of the organic stilbazolium and CLP crystals compared to the inorganic crystals manifests greater THz generation efficiency.

Currently, organic electro-optic crystals having high nonlinear optical properties have to improve or optimize not only nonlinear optical properties but also various crystal properties to achieve high THz wave generation efficiency.

For example, OH1 (2-(3-(4-hydroxystyryl)-5,5-dimethylcyclohex-2-enylidene)malononitrile) and DAST (N,N-dimethylamino-N'-methylstilbazolium 4-methylbenzenesulfonate) crystals having the greatest performance exhibit the highest THz generation efficiency at a wavelength in the infrared (IR) range of 1.0~1.6 μm.

Under such a pump wavelength range, that is, in the near infrared (NIR) range of 0.7~1.0 μm corresponding to an important wavelength range for a commercially available high-power femtosecond Ti:sapphire laser supply source, these crystals show low THz wave generation efficiency by a phase matching condition.

Furthermore, high photochemical stability and a large operating wavelength range are regarded as important, which are related with linear absorption properties of crystals. Therefore, development of organic crystals for THz generation with high efficiency in the NIR range is also important.

DISCLOSURE

Technical Problem

Accordingly, the present invention has been made keeping in mind the problems encountered in the related art, and an object of the present invention is to provide ionic electro-optic quinolinium single crystals able to generate a THz wave with high efficiency.

Technical Solution

In order to accomplish the above object, the present invention provides a quinolinium derivative for use in nonlinear optics so as for THz wave generation, as represented by Chemical Formula 1 or 2 below.

Chemical Formula 1

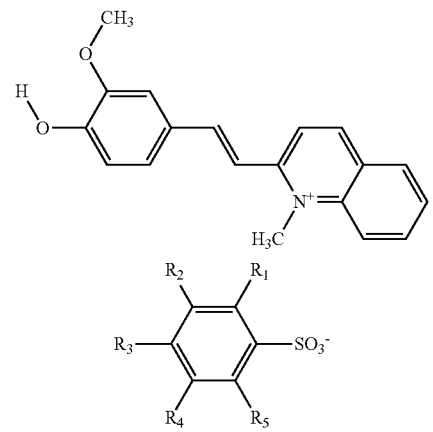

In Chemical Formula 1, $R_1$~$R_5$ are each independently any one selected from the group consisting of hydrogen, hydroxyl, halogen, pseudohalogen, formyl, carboxyl, alkyl, long-chain alkyl, alkoxy, long-chain alkoxy, cycloalkyl, haloalkyl, aryl, arylene, haloaryl, heteroaryl, heteroarylene, heterocycloalkylene, heterocycloalkyl, haloheteroaryl, alkenyl, haloalkenyl, alkynyl, haloalkynyl, keto, ketoaryl, haloketoaryl, ketoheteroaryl, ketoalkyl, haloketoalkyl, ketoalkenyl, haloketoalkenyl, phosphoalkyl, phosphonate, phosphate, phosphine, phosphine oxide, phosphoryl, phosphoaryl, sulfonyl, sulfoalkyl, sulfoarenyl, sulfonate, sulfate, sulfone, amine, polyether, silylalkyl and silylalkyloxy.

Chemical Formula 2

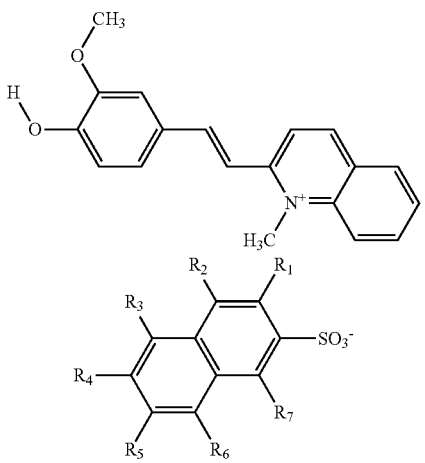

In Chemical Formula 2, $R_1$~$R_7$ are each independently any one selected from the group consisting of hydrogen, hydroxyl, halogen, pseudohalogen, formyl, carboxyl, alkyl, long-chain alkyl, alkoxy, long-chain alkoxy, cycloalkyl, haloalkyl, aryl, arylene, haloaryl, heteroaryl, heteroarylene, heterocycloalkylene, heterocycloalkyl, haloheteroaryl, alkenyl, haloalkenyl, alkynyl, haloalkynyl, keto, ketoaryl, haloketoaryl, ketoheteroaryl, ketoalkyl, haloketoalkyl, ketoalkenyl, haloketoalkenyl, phosphoalkyl, phosphonate, phosphate, phosphine, phosphine oxide, phosphoryl, phosphoaryl, sulfonyl, sulfoalkyl, sulfoarenyl, sulfonate, sulfate, sulfone, amine, polyether, silylalkyl and silylalkyloxy.

Advantageous Effects

According to the present invention, acentric quinolinium derivatives, for example, HMQ-T (2-(4-hydroxy-3-methoxystyryl)-1-methylquinolinium 4-methylbenzenesulfonate), HMQ-MBS (2-(4-hydroxy-3-methoxystyryl)-1-methylquinolinium 4-methoxylbenzenesulfonate), HMQ-NS (2-(4-hydroxy-3-methoxystyryl)-1-methylquinolinium naphthalenesulfonate), HMQ-TMS (2-(4-hydroxy-3-methoxystyryl)-1-methylquinolinium 2,4,6-trimethylbenzenesulfonate), HMQ-OH (2-(4-hydroxy-3-methoxystyryl)-1-methylquinolinium 4-hydroxybenzenesulfonate), and HMQ-HNS (2-(4-hydroxy-3-methoxystyryl)-1-methylquinolinium 6-hydroxy naphthalenesulfonate) can exhibit macroscopic optical nonlinearity based on high molecular orientation, and such quinolinium single crystals can manifest much higher THz generation efficiency even without gloss treatment, compared to existing OH1 and inorganic ZnTe crystals.

BRIEF DESCRIPTION OF DRAWINGS

The patent or application file contains a least one drawing executed in color. Copies of this patent or patent application publication with color drawing(s) will be provided by the Office upon request and payment of the necessary fee.

MODE FOR INVENTION

Figure 1:
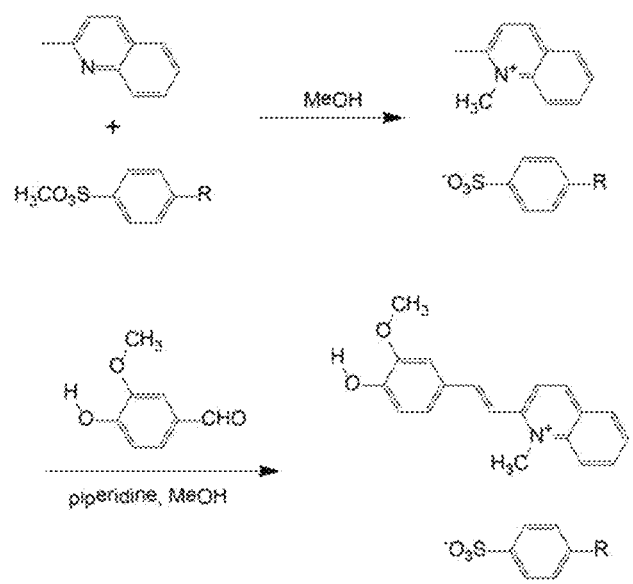
FIG. 1 illustrates a process of synthesizing a quinolinium derivative according to the present invention.

Accordingly, the present invention provides a quinolinium derivative for use in nonlinear optics so as for THz wave generation, as represented by Chemical Formula 1 or 2 below.

Chemical Formula 1

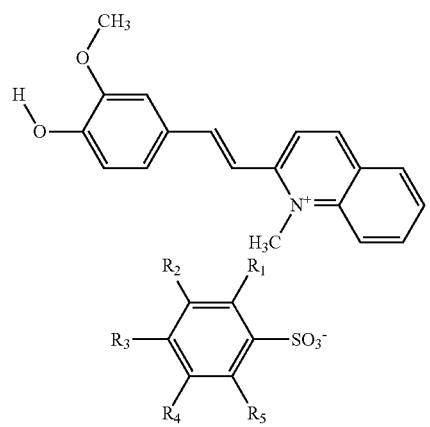

In Chemical Formula 1, $R_1$~$R_5$ are each independently any one selected from the group consisting of hydrogen, hydroxyl, halogen, pseudohalogen, formyl, carboxyl, alkyl, long-chain alkyl, alkoxy, long-chain alkoxy, cycloalkyl, haloalkyl, aryl, arylene, haloaryl, heteroaryl, heteroarylene, heterocycloalkylene, heterocycloalkyl, haloheteroaryl, alkenyl, haloalkenyl, alkynyl, haloalkynyl, keto, ketoaryl, haloketoaryl, ketoheteroaryl, ketoalkyl, haloketoalkyl, ketoalkenyl, haloketoalkenyl, phosphoalkyl, phosphonate, phosphate, phosphine, phosphine oxide, phosphoryl, phosphoaryl, sulfonyl, sulfoalkyl, sulfoarenyl, sulfonate, sulfate, sulfone, amine, polyether, silylalkyl and silylalkyloxy.

Chemical Formula 2

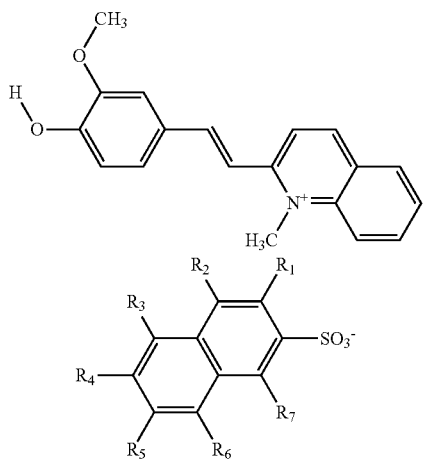

In Chemical Formula 2, $R_1 \sim R_7$ are each independently any one selected from the group consisting of hydrogen, hydroxyl, halogen, pseudohalogen, formyl, carboxyl, alkyl, long-chain alkyl, alkoxy, long-chain alkoxy, cycloalkyl, haloalkyl, aryl, arylene, haloaryl, heteroaryl, heteroarylene, heterocycloalkylene, heterocycloalkyl, haloheteroaryl, alkenyl, haloalkenyl, alkynyl, haloalkynyl, keto, ketoaryl, haloketoaryl, ketoheteroaryl, ketoalkyl, haloketoalkyl, ketoalkenyl, haloketoalkenyl, phosphoalkyl, phosphonate, phosphate, phosphine, phosphine oxide, phosphoryl, phosphoaryl, sulfonyl, sulfoalkyl, sulfoarenyl, sulfonate, sulfate, sulfone, amine, polyether, silylalkyl and silylalkyloxy.

Ionic electro-optic crystals having high optical nonlinearity, such as DAST, DSTMS (N,N-dimethylamino-N'-methyl-stilbazolium 2,4,6-trimethylbenzenesulfonate) and DAPSH (N,N-dimethylamino-N'-phenyl-4-stilbazolium hexafluorophosphate), include a 1,4-dimethylpyridinium or 4-methyl-1-phenylpyridinium salt, but the quinolinium single crystals according to the present invention, for example, 2-(4-hydroxy-3-methoxystyryl)-1-methylquinolinium 4-methylbenzenesulfonate (HMQ-T) in which the anion in Chemical Formula 1 is substituted with $CH_3$, and 2-(4-hydroxy-3-methoxystyryl)-1-methylquinolinium 4-methoxylbenzenesulfonate (HMQ-MBS) in which the anion is $OCH_3$, include a 1-methyl quinolinium salt for an electron acceptor group.

However, electron accepting properties of the 1-methyl quinolinium derivative have not yet been investigated.

Upon electric-field-induced second harmonic (EFISH) measurement using chloroform as a nonpolar solvent, which allows EFISH generation measurement for an ionic material without ionic cation and anion separation, the electron accepting capacity of 1-methyl quinolinium iodide having a (dialkylamino)-bithiophene electron donor group approximates to $\mu\beta_z = 1250 \times 10^{-48}$ [wherein $\beta_z$ is a vector component in a dipole moment $\mu$ direction of a hyperpolarizability tensor $\beta_{ijk}$] and is similar to in a 1,2-dimethylpyridinium salt.

In order to investigate the electron accepting properties of 1-methylquinolinium having a 4-hydroxy-3-metoxybenzene electron donor, the present applicant calculated molecular optical nonlinearity of the 2-(4-hydroxy-3-methoxystyryl)-1-methylquinolinium (HMQ) cation only by way of quantum chemical calculation based on the finite field (FF) density function theory (DFT) using B3LYP/6-311+G*.

With reference to the synthesis mechanism of FIG. 1, the direction of the —O—H group in Chemical Formula 1 may have a great influence on the molecular optical nonlinearity properties including the amplitude and direction of first hyperpolarizability $\beta$. In many cases, the C—O—H plane actually meets a plane of phenyl and methoxy groups. Also in a gas phase, as illustrated in FIG. 1, the direction of the O—H group may be estimated along with hydrogen close to the methoxy group. This is because of a high tendency of forming a strong intramolecular hydrogen bond of O—H . . . OO—$CH_3$. Thus, for quantum chemical calculation of the HMQ cation in a gas phase, the optimized molecular configuration (OPT) was calculated using molecular geometry shown in FIG. 1.

As for the HMQ cation as the designated HMQ (OPT), the present applicant calculated zero-frequency hyperpolarizability tensor $\beta_{ijk}$ by way of the FF method, and evaluated maximum first hyperpolarizability $\beta_{max}$. The results are given in Table 1 below. Also, the detail thereof is given in Table 2 below.

TABLE 1

|  | $\lambda_{max}$ (nm) | $T_m/T_i$ (° C.) | max (OPT) ($10^{-30}$ esu) | max (EXP) ($10^{-30}$ esu) | Order Parameter $\cos^3(\theta_p)$ | $\beta_{iii}^{eff}$ ($10^{-30}$ esu) | $N^2 \langle (\beta^{eff})^2 \rangle$ | Powder SHG | Crystal structure (point group) |
|---|---|---|---|---|---|---|---|---|---|
| HMQ-T | 439 | 273/297 | 145 | 169 | 0.92 | 155 | 0.77 | 0.63 | Monoclinic Pn (m) |
| HMQ-MBS | 441 | 265/291 | 184 | 178 | 1.0 | 178 | 0.94 | 0.23 | Monoclinic Pc (m) |
| DAST | 475 | 250/250 | 159 | 194 | 0.83 | 161 | 1 | 1.0 | Monoclinic Cc (m) |
| OH1 | 426 | 212/325 | 104 | 93 | 0.69 | 63 | 0.3 | 0.5 | Orthorhombic $Pna2_1$ (mm2) |

Table 1 as above shows the physical and structural data results of the HMQ crystal according to the present invention, compared to the DAST and OH1 crystals.

TABLE 2

| | HMQ cation (OPT) | HMQ-T cation (EXP) | HMQ-MBS cation (EXP) | DAST cation (OPT) | DAST cation (EXP) | OH1 (OPT) | OH1 (EXP) |
|---|---|---|---|---|---|---|---|
| $\beta_{xxx}$ | 0.61 | 0.23 | 0.03 | −0.11 | −0.21 | −0.25 | −0.07 |
| $\beta_{xxy}$ | 0.64 | −0.27 | 0.16 | −0.04 | 0.03 | −0.35 | −0.23 |
| $\beta_{xyy}$ | 0.58 | 0.15 | −0.35 | 0.05 | −0.05 | −0.56 | −1.52 |
| $\beta_{yyy}$ | 0.07 | −0.32 | 0.71 | −0.42 | −0.06 | −9.02 | −24.31 |
| $\beta_{xxz}$ | 3.09 | 1.32 | 1.31 | 0.18 | 0.25 | −0.30 | −0.37 |
| $\beta_{xyz}$ | 3.20 | −1.02 | −2.54 | 0.00 | 0.38 | 1.64 | 1.90 |
| $\beta_{yyz}$ | 2.53 | 0.88 | 9.18 | −4.85 | −3.89 | 21.14 | 30.87 |
| $\beta_{xzz}$ | 17.44 | 8.44 | −8.44 | 0.38 | −1.28 | −3.16 | −2.30 |
| $\beta_{yzz}$ | 25.06 | −19.43 | 40.44 | −2.59 | −3.86 | −40.98 | −35.54 |
| $\beta_{zzz}$ | 134.25 | 164.95 | 162.54 | 158.76 | 193.60 | 65.49 | 36.13 |
| $\beta_{max}$ | 145 | 169 | 178.4 | 159.05 | 193.85 | 103.73 | 92.57 |

As is apparent from Table 1, the HMQ cation has relatively weaker phenolic and methoxy electron donors compared to a typical dimethylamino electron donor, but the HMQ (OPT) cation having a 1-methoxyquinolinium electron acceptor exhibits a high maximum first hyperpolarizability $\beta_{max}$ of $145 \times 10^{-30}$ esu, which is similar to the DAST cation ($159 \times 10^{-30}$ esu) having a 1,4-dimethylpyridinium electron acceptor and a dimethylamino electron donor and is greater than the OH1 molecule ($104 \times 10^{-30}$ esu). The 1-methylquinolinium derivative having the dimethylamino electron donor as in the DAST cation exhibits higher maximum first hyperpolarizability $\beta_{max}$ ($184 \times 10^{-30}$ esu) compared to the DAST cation, which means that the electron accepting capacity of 1-methylquinolinium is greater than any one of widely used 1,4-dimethylpyridinium acceptors.

Therefore, HMQ having the 1-methylquinolinium acceptor and derivatives thereof are preferable in terms of nonlinear optical applications including THz wave generation, and may exhibit vastly superior effects.

Accordingly, methathesized synthesis of HMQ-T and HMQ-MBS and obtained crystal structures thereof have been reported, but reports for so superior results using these materials, including linear and nonlinear optical properties, physical properties including bulk crystal growth and THz wave generation and application thereof, are not yet known. Hence, the present invention pertains to applications of such materials to nonlinear optics and THz wave generation and to an optimal preparation method thereof.

Below is a description of a method of preparing the quinolinium derivative according to the present invention.

The HMQ derivative may be synthesized through the following two methods: specifically, 1) as reported as above, methathesis of 2-(4-hydroxy-3-methoxystyryl)-1-methylquinolinium iodine (HMQ-I) and silver (I) methylbenzenesulfonate for HMQ-T; and 2) as shown in FIG. 1, condensation of vanilin using dimethylquinolinium 4-methoxylbenzenesulfonate for HMQ-MBS and dimethylquinolinium 4-methylbenzenesulfonate for HMQ-T.

However, because of low solubility (0.14 g/100 g methanol) of HMQ-I in methanol as a reaction solvent, a large quantity of methathesis necessary for bulk crystal growth may become comparatively difficult, and furthermore, in many cases, physical properties of a phenolic p-conjugated material are very sensitive to impurities and environmental conditions. Moreover, residual silver (I) iodide accompanied by methathesis may cause changes in physical and optical properties in solution and solid states.

Also, the crystalline material obtained by methathesis is blackish brown colored, whereas the color of the crystalline material obtained by condensation is light orange.

Furthermore, a dark brown HMQ-T crystalline material recrystallized from methanol after methathesized synthesis in HMQ-T exhibits a different powder X-ray diffraction (XRD) pattern compared to reported crystal structures, and thereby appears to have polymorphism.

Thus, the quinolinium derivative according to the present invention is preferably synthesized through a condensation reaction as shown in FIG. 1 so as for characterization and crystal growth for use in nonlinear optics and THz wave generation. Nevertheless, as will be described later, the present inventors effectively synthesized a quinolinium derivative through condensation and methathesis.

The physical and structural data results of the HMQ derivative synthesized by condensation are as shown in Table 1.

As seen in Table 1, as for absorption properties of the HMQ derivative in a methanol solution, HMQ-T and HMQ-MBS are greater in maximum absorption wavelength $\lambda_{max}$ than OH1, but are much lower than DAST.

In acetonitrile as a different solvent, the maximum absorption wavelength $\lambda_{max}$ (426 nm for HMQ-T and 428 nm for HMQ-MBS) is much lower than that of DAST (471 nm).

The low absorption behavior of the HMQ derivative showing comparatively large molecular nonlinearity may be favorable when used as a nonlinear optical or THz wave light source in consideration of photochemical stability and higher transparency.

As results of measurement of thermal properties of the quinolinium derivative according to the present invention using differential scanning calorimetry (DSC) and thermogravimetric analysis (TGA) at a scanning rate of 10° C./min, the thermal weight-loss temperature $T_i$ was estimated as a temperature at the intercept of the leading edge of the weight loss by the baseline of TGA scans.

Figure 2:
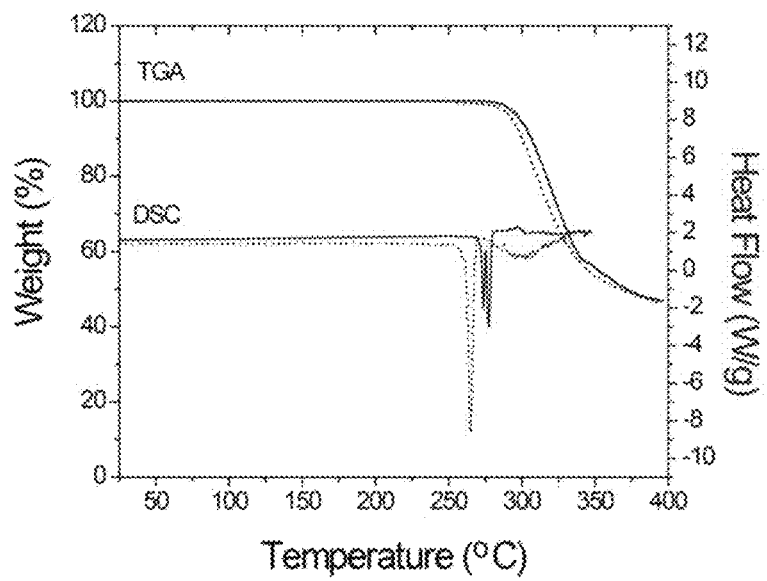
FIG. 2 illustrates a graph of thermal properties of the quinolinium derivative according to the present invention.

As shown in FIG. 2, the HMQ-T crystal manifests high thermal stability exceeding 290° C., which is higher than 260° C. of the DAST crystal. Also, as measured using the peak position upon DSC scanning, the melting temperature $T_m$ is 273° C. for HMQ-T and 265° C. for HMQ-MBS, which are higher compared to DAST ($T_m$=256° C.)

Figure 3:
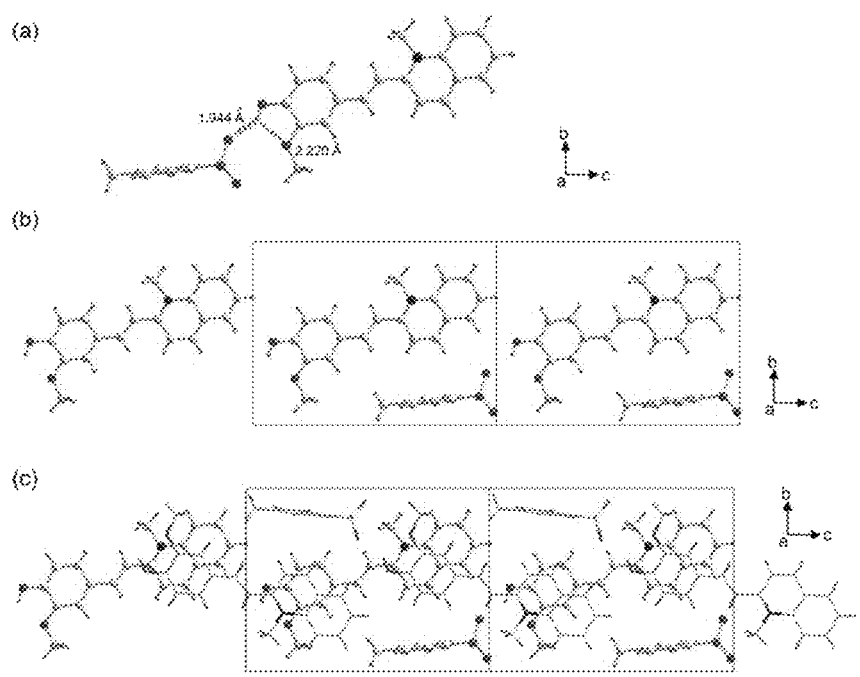
FIGS. 3 and 4 illustrate results of X-ray structural analysis of nonlinear optical crystals of Examples 1 and 2.
Figure 4:
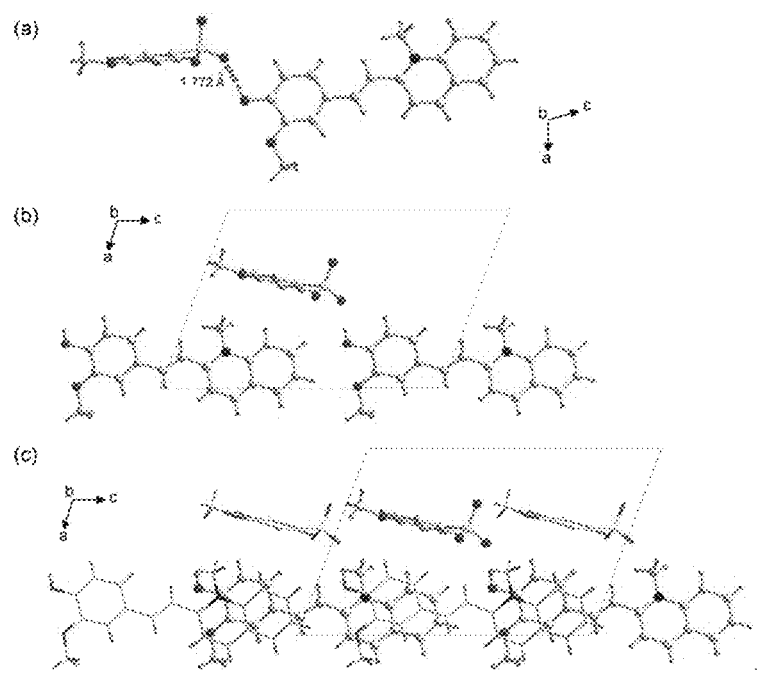

As for macroscopic optical nonlinearity of quinolinium single crystals according to the present invention, the results of X-ray structural analysis of the crystals are shown in FIGS. 3 and 4.

FIGS. 3 and 4 illustrate molecular configurations of HMQ-T and HMQ-MBS crystals and crystal packing diagrams. The HMQ-T and HMQ-MBS crystals respectively indicate monoclinic Pn and Pc space groups having point groups m.

As illustrated in (a) of FIGS. 3 and (a) of FIG. 4, the main supramolecular interactions of HMQ-T and HMQ-MBS crystals as in the —O—H . . . O—S— group having an O . . . O distance of about 2.66 Å for HMQ-T and about 2.65 Å for HMQ-MBS have not only a strong Coulomb force between the 1-methylquinolinium cation and the sulfonate group but also a strong hydrogen bond between the phenolic OH group and the sulfonate group.

As illustrated in (b) of FIGS. 3 and (b) of FIG. 4, the HMQ cation-anion pair constitutes an acentric polar layer formed side by side ((c) of FIGS. 3 and (c) of FIG. 4).

Furthermore, in order to evaluate the effect of different molecular geometry having a different tilting angle at a p-conjugated bridge and a different direction of the O—H group in a solid state of the quinolinium derivative according to the present invention, macroscopic nonlinearity of the HMQ cation (EXP) was calculated, as measured by single X-ray structural analysis in individual crystals based on the density function theory using the FF method.

The results of maximum first hyperpolarizability $\beta_{max}$ are shown in Table 1 and the detail thereof is given in Table 2.

In two EXP forms in the crystal, the maximum first hyperpolarizability $\beta_{max}$ is slightly increased compared to the optimized molecule of HMQ (OPT), and compared to the OPT molecule having $145 \times 10^{-30}$ esu, HMQ-T (EXP) has $169 \times 10^{-30}$ esu and HMQ-MBS (EXP) has $178 \times 10^{-30}$ esu, and a difference between two crystal forms is relatively low.

The HMQ cation has a different direction of the electron donor OH group in a solid state, and is still in the same plane as in a phenyl ring but is maintained in macroscopic optical nonlinearity.

In the case where the nonlinear optical chromophore has the asymmetric configuration or position of the electron donor and the acceptor is not accurate at each terminal of the long axis of the molecule, the long axis of the molecule cannot be simply estimated as the main direction of the first hyperpolarizability $\beta_{max}$ corresponding to the important information for evaluation of macroscopic optical nonlinearity.

Although the position of nitrogen atom (N+) in the quinolinium acceptor of the HMQ cation is not at the terminal, it is at the side of the long axis of the molecule, and thus based on the detail of FF calculation shown in Table 2 of SI, the maximum first hyperpolarizability of the HMQ cation is evaluated. In the case where the nonlinear optical chromophore having has the asymmetric configuration or position of the electron donor and the acceptor is not accurate at each terminal of the long axis of the molecule, the long axis of the molecule cannot be simply estimated as the main direction of the first hyperpolarizability $\beta_{max}$ corresponding to the important information for evaluation of macroscopic optical nonlinearity.

Figure 5:
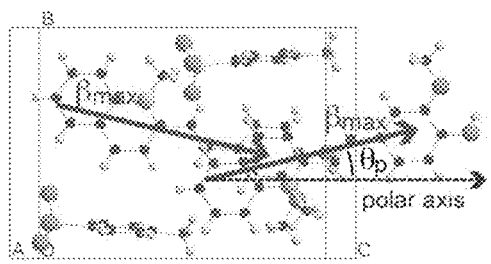
FIG. 5 illustrates results of evaluation of the direction of maximum first hyperpolarizability $\beta_{max}$ of the HMQ cation.
Figure 5:
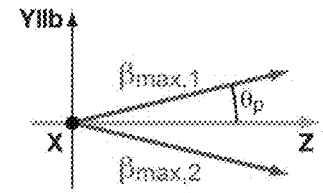
Figure 5:
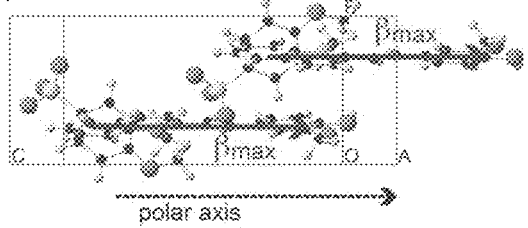
Figure 5:
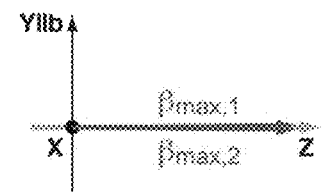

Although the position of nitrogen atom (N+) in the quinolinium acceptor of the HMQ cation is not at the terminal, it is at the side of the long axis of the molecule, and thus based on the detail of FF calculation shown in Table 2 of SI, the direction of the maximum first hyperpolarizability $\beta_{max}$ of the HMQ cation is evaluated. The obtained direction is illustrated in FIG. 5, which indicates the projections on the YZ plane of a Cartesian XYZ system.

In the selected Cartesian XYZ system, the Y axis is parallel to the crystallographic (symmetric) b axis and the Z axis in the ac crystallographic plane is along the polar axis of the crystal, or more accurately is along the main charge transfer axis of the crystal. In both kinds of crystals, the polar axis Z is almost parallel to the c crystallographic axis as shown in FIG. 5.

The angle $\theta_p$ between the main charge transfer axis of the crystal and the maximum first hyperpolarizability $\beta_{max}$ of the molecule approximates to zero. Specifically, $\theta_p$ equals to 13.8° in HMQ-T and equals to 0.5° in HMQ-MBS.

This means that, in both kinds of crystals, the chromophore is nearly perfectly aligned parallel to the orientation approximating to 1.0. In HMQ-T, $\cos^3(\theta_p)$ equals to 0.92 and equals to 1.0 in HMQ-MBS, which are higher than both DAST and OH1 crystals shown in Table 1. This alignment optimizes a diagonal nonlinear optical component and is very preferable for THz wave generation.

Taking into consideration all the hyperpolarizability tensor components $\beta_{max}$ calculated by the FF method and the orientation of the chromophore in the crystallographic system, the present applicant calculated the diagonal component and the off-diagonal component of the effective hyperpolarizability tensor $\beta_{ijk}^{\text{eff}} \propto \chi_{ijk}^{(2)}$ in the Cartesian XYZ system. The diagonal components of the effective hyperpolarizability tensor $\beta_{ijk}^{\text{eff}}$ are listed in Table 1, and the other non-zero off-diagonal components are listed in SI of Table 2. Because of high-order parameter approximating to 1.0, the off-diagonal components of HMQ-T and HMB-MBS may be ignored.

HMQ-T and HMQ-MBS crystals respectively exhibit large diagonal components of effective hyperpolarizability tensor $\beta_{333}^{\text{eff}} = 154 \times 10^{-30}$ esu and $178 \times 10^{-30}$ esu, which are higher than DAST ($161 \times 10^{-30}$ esu) and OH1 ($63 \times 10^{-30}$ esu) crystals.

So as for screening of macroscopic optical nonlinearity, the present applicant performed second harmonic generation (SHG) testing of powder at a non-resonant fundamental wavelength of 1.9 μm. The SHG efficiency was measured from the well-characterized ionic DAST crystal. HMQ-T and HMQ-MBS crystalline powders exhibit large macroscopic nonlinearity about 0.62 times and 0.23 times the SHG efficiency of the DAST powder.

Also, by considering number density of chromophores N and averaged contribution for the different orientation of crystallite regarding the corresponding point group symmetry, it is possible to evaluate the power testing efficiency theoretically estimated from the effective hyperpolarizability tensor component $\beta_{ijk}^{\text{eff}}$.

Although the obtained figure, $N^2 \langle (\beta^{\text{eff}})^2 \rangle$ is insignificant for contribution to intermolecular interactions in the crystal as well as possible phase matching enhancement, it mostly provides a good first estimate for predicted macroscopic nonlinear optical properties.

As for $N^2 \langle (\beta^{\text{eff}})^2 \rangle$ of OH1, HMQ-T is 2.6 times the OH1 and HMQ-MBS is 3.2 times the OH1, wherein such two values are much higher than experimentally measured values. However, the chromophore having OH group may be very sensitive to environmental conditions, and for example, the macroscopic hyperpolarizability of the OH1 chromophore may be different by a factor of 2 in a different solvent.

The $N^2 \langle (\beta^{\text{eff}})^2 \rangle$ figure of merit of OH1 is about 30% of DAST, but is almost doubled in experimentally measured powder testing.

With respect to DAST, $N^2 \langle (\beta^{\text{eff}})^2 \rangle$ of HMQ-T is 76%, which is remarkably consistent with the experimental powder testing efficiency for DAST.

On the other hand, in HMQ-MBS, the experimental and theoretical values are different by a factor of 3.7 from DAST. This inconsistency may result in a great environmental effect of macroscopic nonlinearity of the HMQ chromophore on environment.

Figure 11:
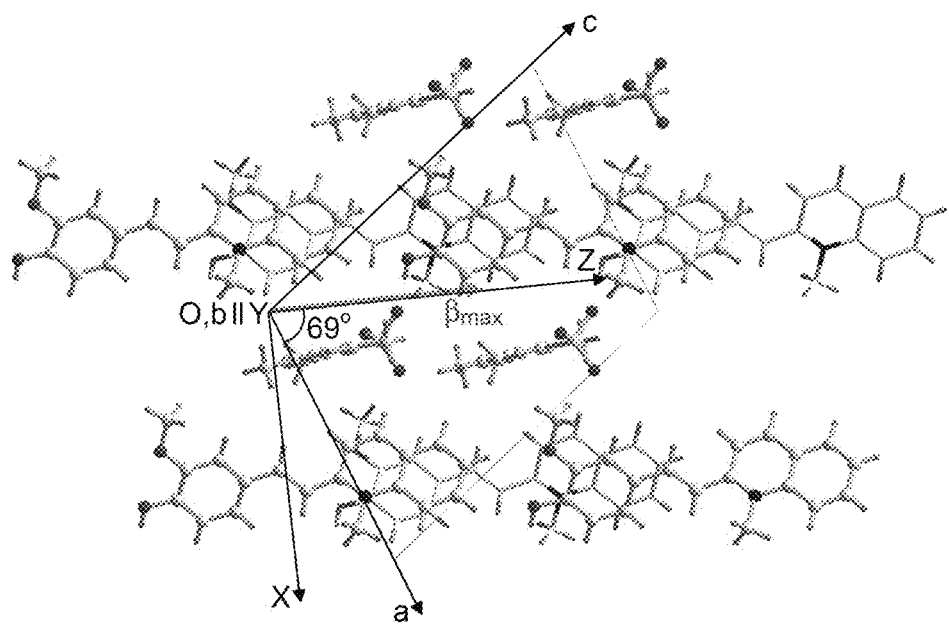
FIG. 11 illustrates results of X-ray structural analysis of HMQ-TMS, that is, results of evaluation of the direction of maximum first hyperpolarizability $\beta_{max}$ of the cation.

The results of evaluation of the direction of $\beta_{max}$ of the HMQ-TMS crystal are shown in FIG. 11. As shown in this drawing, the angle $\theta_p$ between $\beta_{max}$ and Z axis is 1.1°, and $\cos^3(\theta_p)$ equals to 1.0.

As mentioned above, novel quinolinium derivative crystals according to the present invention can be seen to exhibit superior second nonlinear optical properties compared to currently preferably known DAST and OH1, and to provide excellent effects when used for THz generation and nonlinear optics.

Figure 6:
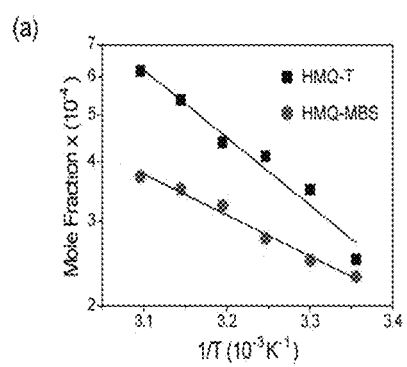
FIG. 6 illustrates the solubility in methanol of the quinolinium derivative according to the present invention.
Figure 6:
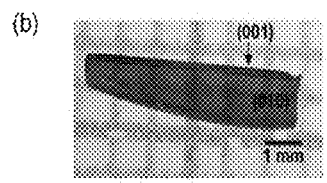
Figure 6:
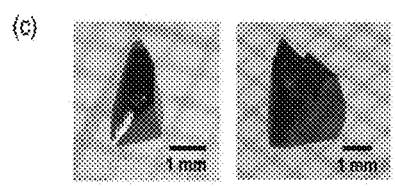

Meanwhile, the solubility in methanol of the quinolinium derivative according to the present invention is illustrated in (a) of FIG. 6. As is apparent from this graph, HMQ-T is higher in solubility than HMQ-MBS. Specifically, HMQ-T shows 0.89 g/100 g methanol at 50° C. and HMQ-MBS manifests 0.56 g/100 g methanol. The solid line in the graph is based on the known Van't Hoff thermodynamic equilibrium equation using an ideal solution.

Figure 12:
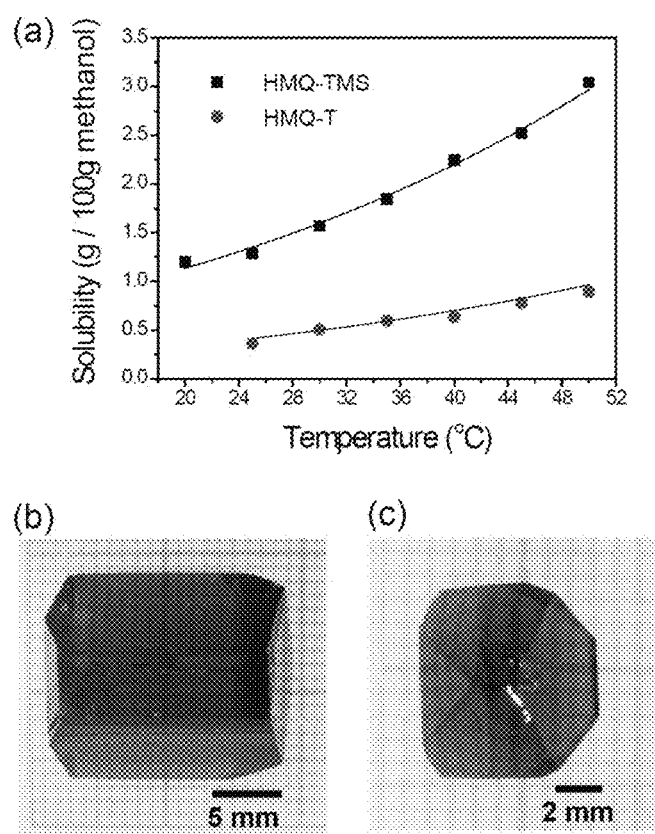
FIG. 12 illustrates the solubility in methanol of HMQ-TMS according to the present invention and the crystal images.

The solubility results of HMQ-TMS and HMQ-T are illustrated in (a) of FIG. 12. HMQ-TMS is higher in solubility than HMQ-T.

Also, the present applicant grew bulk HMQ-T and HMQ-MBS single crystals by way of a slow cooling process in methanol at cooling rate of 1° C./day from 40° C.

In both kinds of crystals, the first nucleate appeared at about 25~26° C.

Typical as-grown HMQ-T and HMQ-MBS crystals are yellow colored as shown in (b) and (c) of FIG. 6, respectively, which are brighter than the orange-red OH1 crystal as well as the dark red DAST crystal. The as-grown HMQ-T crystal has a flat and parallel surface with good optical quality, but the HMQ-MBS crystal has a more complicated form.

In FIG. 6, (b) shows the form of the as-grown HMQ-T crystal as evaluated by X-ray diffraction, wherein the parallel surface is along the b crystallographic plane, which means that the polar c-axis is on the plane as shown in (b) of FIG. 6. Thus, when compared to the form of the HMQ-MBS crystal having a non-parallel surface, the as-grown HMQ-T crystal is more preferable for THz wave generation.

The as-grown HMQ-TMS crystal is illustrated in (b) and (c) of FIG. 12.

Depending on the properties of the crystals including morphology, the HMQ-T crystal is selected for characterization of THz wave generation testing and physical properties. The results thereof as compared with the THz generator OH1 crystal are illustrated in FIG. 7.

Figure 7:
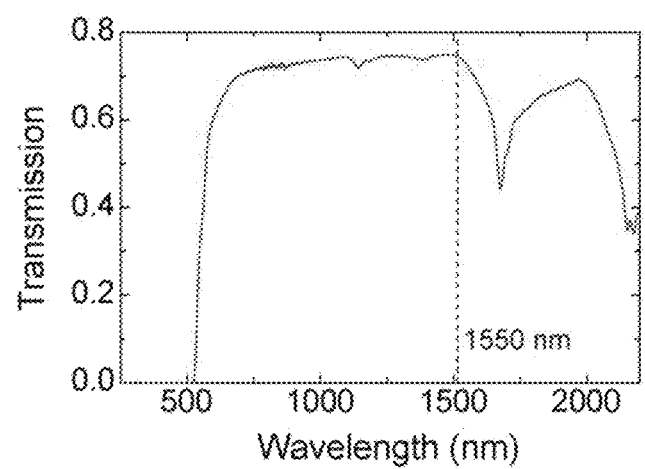
FIG. 7 illustrates the transmission spectrum using the HMQ-T crystal according to the present invention.

FIG. 7 illustrates the transmission spectrum of the 0.12 mm thick HMQ-T crystal (b-plate) without gloss treatment using incident normal non-polarized light.

The cut-off wavelength $\lambda_{cut-off}$ of HMQ-T according to the present invention is about 595 nm, which is much shorter than OH1 (~640 nm) and DAST (~680 nm) crystals.

The lower cut-off wavelength $\lambda_{cut-off}$ may be desirable in terms of 1) photochemical stability, and 2) a higher transparency range and thus a wider operating wavelength range.

The HMQ-T crystal according to the present invention possesses vibrational resonance overtones at about 1675 nm and low absorbability at 1550 nm, but applicability thereof is limited at such a theoretically important wavelength due to comparatively strong absorbability of the OH1 crystal at about 1550 nm.

Ultimately, the HMQ-T crystal according to the present invention has higher transparency ranging from 595 nm to 1550 nm compared to OH1 in the range of 640~1400 nm.

Figure 13:
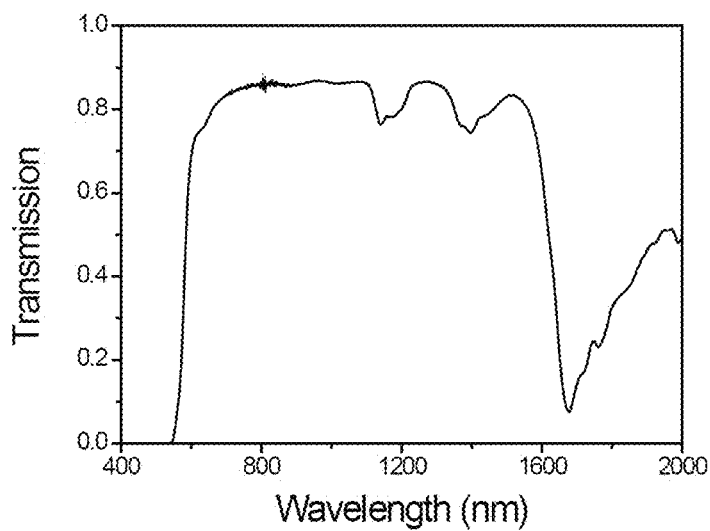
FIG. 13 illustrates the transmission spectrum using the HMQ-TMS crystal according to the present invention.

Meanwhile, the transmission spectrum of HMQ-TMS is illustrated in FIG. 13. This is the transmission spectrum of the HMQ-TMS crystal having a thickness of 2.34 mm without surface treatment.

The fundamental wavelength of 1550 nm may be very usefully applied to a laser pump supply source which may be diversely utilized at such a wavelength, for example, a femtosecond laser for THz wave generation and a CW telecommunication laser for electro-optic applications.

Below, the present invention is described in more detail through the following specific examples.

In the present examples and comparative example, a THz wave was generated by use of optical rectification (OR) with femtosecond laser pump pulses in a variety of nonlinear optical crystals, and was detected using an electro-optic sampling (EOS) method.

Produced from a regenerative amplified Ti:sapphire laser, fundamental optical pulses having a duration of 170 fs at 836 nm at a repetition rate of 1 kHz were used.

In the case of all the generation materials, the same THz electro-optic detector ZnTe crystal was used, and measurement was performed at room temperature in air with a humidity of 28%.

2-methylquinoline and vanilin for condensation synthesis routes as illustrated in FIG. 1 were commercially available from Sigma-Aldrich without further purification. $^1$H-NMR data was recorded on Varian 400 MHz. All chemical shifts were recorded at ppm ($\delta$) for $(CH_3)_4Si$.

Example 1

To synthesize 2-(4-hydroxy-3-methoxystyryl)-1-methylquinolinium 4-methylbenzenesulfonate (HMQ-T), methyl p-toluenesulfonate (32.34 ml, 0.21 mol (98%)) and 2-methylquinoline (29.8 ml, 0.21 mol (95%)) were dissolved in methanol (50 ml), and the resulting solution was stirred at 50° C. for one day.

The colorless solution turned light pink. The solution was cooled to room temperature, methanol was evaporated, and 1,2-dimethoxyethanol was added to thus obtain a precipitate, after which white-pink powder of 1,2-dimethylquinolinium 4-methylbenzene sulfonate was obtained through filtration and then dried in a vacuum oven at 60° C.

1,2-dimethylquinolinium 4-methylbenzenesulfonate (40 g, 0.121 mol) and vanilin (18.5 g, 0.121 mol) were dissolved in methanol (100 ml).

A catalyst piperidine (2.4 ml, 0.0242 mol) was added with stirring under reflux for three days. The resulting solution was cooled to room temperature, and then orange crystal powder was obtained. A final product was obtained through recrystallization in methanol and then dried in a vacuum oven at 60° C. for 1 hr.

In this example, the HMQ-T crystal having a surface with a thickness of 0.56 mm was used for THz generation. Because of comparatively high optical quality of the crystal having a flat surface, as-grown HMQ-T was used without gloss treatment.

$^1$H-NMR (400 MHz, $CD_3OD$, $\delta$): 8.83 (d, 1H, J=8.8, $C_5H_2N$), 8.44 (d, 1H, J=9.2, $C_6H_4$), 8.40 (d, 1H, J=8.8, $C_5H_2N$), 8.24 (d, 1H, J=8.0, $C_6H_4$), 8.15 (m, 1H, $C_6H_4$), 8.06 (d, 1H, J=15.6, CH), 7.90 (m 1H, $C_6H_4$), 7.69 (d, 1H, J=15.2, CH), 7.68 (d, 2H, J=6.4, $C_6H_4SO_3^-$), 7.52 (s, 1H, $C_6H_3$), 7.39 (dd, 1H, $C_6H_3$), 7.20 (d, 2H, J=8.4, $C_6H_4SO_3^-$), 6.91 (d, 1H, J=8.0, $C_6H_3$), 4.57 (s, 3H, OMe), 4.00 (s, 3H, Me), 2.36 (s, 3H, NMe). Elemental analysis for $C_{26}H_{25}NO_5S$, Calcd.: C, 67.37; H, 5.43; N, 3.02; S, 6.92. Found: C, 67.40; H, 5.53; N, 3.02; S, 7.02.

Example 2

To synthesize 2-(4-hydroxy-3-methoxystyryl)-1-methylquinolinium 4-methoxylbenzenesulfonate (HMQ-MBS), methyl 4-methoxybenzene sulfonate (10 g, 0.049 mol) and 2-methylquinoline (6.67 ml, 0.049 mol (98%)) were dissolved in methanol (30 ml), and the resulting solution was stirred at 50° C. for four days. The colorless solution turned light pink. Subsequently, methanol was evaporated, and 1,2-dimethoxymethanol was added to thus obtain a precipitate.

White-pink powder of 1,2-dimethylquinolinium 4-methoxylbenzenesulfonate was obtained through filtration and then dried in a vacuum oven at 60° C.

1,2-dimethylquinolinium 4-methoxylbenzenesulfonate (9 g, 0.026 mol) and vanilin (3.96 g, 0.026 mol) were dissolved in methanol (100 ml).

A catalyst piperidine (1 ml, 0.01 mol) was added with stirring under reflux for four days. The resulting solution was cooled to room temperature, and then orange-brown crystalline powder was obtained.

A final product was obtained through recrystallization in acetone and then dried in a vacuum oven at 60° C. for 1 hr.

$^1$H-NMR (400 MHz, CD$_3$OD, δ): 8.81 (d, 1H, J=8.8, C$_5$H$_2$N), 8.42 (d, 1H, J=8.8, C$_6$H$_4$), 8.38 (d, 1H, J=9.2, C$_6$H$_4$), 8.22 (d, 1H, J=8.0, C$_5$H$_2$N), 8.13 (m, 1H, C$_6$H$_4$), 8.05 (d, 1H, J=15.6, CH), 7.88 (m 1H, C$_6$H$_4$), 7.72 (m, 2H, C$_6$H$_4$SO$_3^-$), 7.66 (d, 1H, J=16.0, CH), 7.50 (s, 1H, C$_6$H$_3$), 7.38 (dd, 1H, C$_6$H$_3$), 6.91 (m, 2H, C$_6$H$_4$SO$_3^-$), 6.89 (m, 1H, C$_6$H$_3$), 4.55 (s, 3H, NMe), 4.00 (s, 3H, OMe), 3.80 (s, 3H, OMe). Elemental analysis for C$_{26}$H$_{25}$NO$_6$S, Calcd.: C, 65.12; H, 5.25; N, 2.92; S, 6.69. Found: C, 65.19; H, 5.21; N, 2.94; S, 6.78.

Example 3

To synthesize 2-(4-hydroxy-3-methoxystyryl)-1-methylquinolinium naphthalene-2-sulfonate (HMQ-NS), crystalline powder was obtained in the same manner as in Example 1, with the exception that 1,2-dimethylquinolinium naphthalene-2-sulfonate was used instead of 1,2-dimethylquinolinium 4-methylbenzenesulfonate.

Example 4

Synthesis of methyl 2,4,6-trimethylbenzenesulfonate: to a solution of 2,4,6-trimethylbenzene-1-sulfonyl chloride (30 g, 0.136 mol) dissolved in methanol (350 ml), a solution of NaOH (5.49 g, 0.136 mol, 1 equiv.) dissolved in methanol (60 ml) was added dropwise. White NaCl was precipitated and filtered to remove NaCl, and the filtered solution was evaporated, followed by extraction with water and methylene chloride, and the organic layer was obtained, evaporated the solvent therefrom and then dried in a vacuum, affording a white solid at a yield of 96%.

$^1$H-NMR (400 MHz, CDCl$_3$, δ): 6.98 (s, 2H, C$_6$H$_2$SO$_3^-$), 3.69 (s, 3H, SO$_3^-$CH$_3$), 2.62 (s, 6H, 2CH$_3$), 2.31 (s, 3H, CH$_3$).

Synthesis of 1,2-dimethylquinolinium 2,4,6-trimethylbenzenesulfonate: 2-methylquinoline (18.5 ml, 0.130 mol) and methyl 2,4,6-trimethylbenzenesulfonate (27.82 g, 0.130 mol, 1 equiv.) were dissolved in 1,2-dimethoxyethane and stirred at 70° C. for four days. The solution became violet-colored and the white solid was precipitated. The solution was filtered, and the filtered solution was dried in a vacuum oven at 50° C., affording light pink powder at a yield of 50%.

$^1$H-NMR (400 MHz, CDCl$_3$, δ): 8.68 (d, 1H, J=8.4, C$_5$H$_2$N), 8.42 (d, 1H, J=8.8, C$_6$H$_4$), 8.11 (d, 1H, J=8.0, C$_6$H$_4$), 8.10 (m, 1H, C$_6$H$_4$), 7.85 (d, 1H, J=8.4, C$_5$H$_2$N), 7.84 (t, 1H, J=7.8, C$_6$H$_4$), 6.65 (s, 2H, C$_6$H$_2$SO$_{31}$, 4.69 (s, 3H, NCH$_3$), 3.26 (s, 3H, CH$_3$), 2.47 (s, 6H, 2CH$_3$), 2.16 (s, 3H, CH$_3$).

Synthesis of HMO-TMS: 1,2-dimethylquinolinium 2,4,6-trimethylbenzenesulfonate (22 g, 61.54 mmol) and vanilin (9.46 g, 061.54 mmol, 1 equiv.) were dissolved in methanol (160 ml), added with a catalyst piperidine (1.2 ml, 12.31 mmol, 0.2 equiv.) and refluxed at 70° C. for three days. The blackish brown solution was cooled to room temperature and then filtered. A final product was obtained through recrystallization in methanol and then dried in a vacuum oven at 50° C., affording brown powder at a yield of 51%.

$^1$H-NMR (400 MHz, CD$_3$OD, δ): 8.82 (d, 1H, J=9.2, C$_5$H$_2$N), 8.43 (d, 1H, J=9.2 Hz, C$_6$H$_4$), 8.39 (d, 1H, J=8.8 Hz, C$_5$H$_2$N), 8.24 (d, 1H, J=8.2 Hz, C$_6$H$_4$), 8.15 (m, 1H, C$_6$H$_4$), 8.06 (d, 1H, J=15.6 Hz, CH), 7.90 (t, 1H, J=7.4 Hz, C$_6$H$_4$), 7.67 (d, 1H, J=16.0 Hz, CH), 7.52 (s, 1H, C$_6$H$_3$), 7.39 (dd, 1H, C$_6$H$_3$), 6.91 (d, 1H, J=8.0 Hz, C$_6$H$_3$), 6.83 (s, 2H, C$_6$H$_2$SO$_3^-$), 4.56 (s, 3H, NCH$_3$), 3.98 (s, 3H, OCH$_3$), 2.60 (s, 6H, 2CH$_3$). 2.21 (s, 3H, CH$_3$). Elemental analysis for C$_{28}$H$_{29}$NO$_5$S: Calcd. C, 68.41; H, 5.94; N, 2.85; S, 6.52. Found C, 68.48; H, 5.87; N, 2.89; S, 6.38.

Example 5

Synthesis of HMQ-OH: to a solution of HMQ-I (0.53 g, 1.26 mmol) dissolved in methanol (380 ml), a solution of sodium (I) 4-hydroxybenzenesulfonate (0.88 g, 3.79 mmol, 3 equiv.) dissolved in methanol (60 ml) was added dropwise. The reaction solution was cooled to room temperature and then filtered. A final product was obtained through recrystallization in methanol and then dried in a vacuum oven at 60° C., affording orange powder at a yield of 45%.

$^1$H-NMR (400 MHz, DMSO-d$_6$, δ): 10.02 (s, 1H, OH), 9.43 (s, 1H, OH), 8.94 (d, 1H, J=9.2, C$_5$H$_2$N), 8.51 (d, 1H, J=9.2 Hz, C$_6$H$_4$), 8.50 (d, 1H, J=9.2 Hz, C$_5$H$_2$N), 8.29 (d, 1H, J=8.0 Hz, C$_6$H$_4$), 8.17 (d, 1H, J=15.6 Hz, CH), 8.12 (m, 1H, C$_6$H$_4$), 7.90 (t, 1H, J=7.6 Hz, C$_6$H$_4$), 7.70 (d, 1H, J=15.6 Hz, CH), 7.59 (s, 1H, C$_6$H$_3$), 7.41 (dd, 1H, C$_6$H$_3$), 7.37 (d, 2H, J=6.8 Hz, C$_6$H$_4$SO$_3^-$) 6.91 (d, 1H, J=8.4 Hz, C$_6$H$_3$) 6.87 (d, 2H, J=8.8 Hz, C$_6$H$_4$ SO$_{31}$, 4.52 (s, 3H, NCH$_3$), 3.89 (s, 3H, OCH$_3$). Elemental analysis for C$_{25}$H$_{23}$NO$_6$S: Calcd. C, 62.44; H, 5.34; N, 2.86; S, 6.54. Found C, 64.33; H, 5.08; N, 3.01; S, 6.85.

Example 6

Synthesis of HMQ-HNS: a final product was obtained at a yield of 41% in the same manner as in Example 5, with the exception that sodium (I) 6-hydroxynaphthalenesulfonate was used instead of sodium (I) 4-hydroxybenzenesulfonate.

$^1$H-NMR (400 MHz, DMSO-d$_6$, δ): 10.06 (s, 1H, OH), 9.75 (s, 1H, OH), 8.95 (d, 1H, J=8.8, C$_5$H$_2$N), 8.52 (d, 1H, J=9.2 Hz, C$_6$H$_4$), 8.51 (d, 1H, J=8.8 Hz, C$_5$H$_2$N) 8.29 (d, 1H, J=8.0 Hz, C$_6$H$_4$), 8.17 (d, 1H, J=15.2 Hz, CH), 8.12 (m, 1H, C$_6$H$_4$), 7.96 (s, 1H, C$_{10}$H$_6$SO$_3^-$) 7.90 (t, 1H, J=7.4 Hz, C$_6$H$_4$), 7.76 (d, 1H, J=8.4 Hz, C$_{40}$H$_6$SO$_3^-$), 7.71 (d, 1H, J=15.6 Hz, CH), 7.60 (s, 1H, C$_{10}$H$_6$SO$_3^-$) 7.56 (s, 1H, C$_6$H$_3$), 7.55 (m, 1H, C$_{10}$H$_6$SO$_3^-$) 7.41 (dd, 1H, C$_6$H$_3$), 7.05 (m, 2H, C$_{10}$H$_6$SO$_3^-$) 6.91 (d, 1H, J=8.0 Hz, C$_6$H$_3$), 4.52 (s, 3H, NCH$_3$), 3.89 (s, 3H, OCH$_3$) Elemental analysis for C$_{29}$H$_{25}$NO$_6$S: Calcd. C, 67.56; H, 4.88; N, 2.72; S, 6.22. Found C, 67.60; H, 4.88; N, 2.78; S, 6.27.

Example 7

Synthesis of HMQ-TMS: to a solution of HMQ-I (0.80 g, 1.92 mmol) dissolved in methanol (650 ml), a solution of silver (I) 2,4,6-trimethylbenzenesulfonate (0.59 g, 1.92 mmol, 1 equiv.) dissolved in methanol (50 ml) was added dropwise. The AgI precipitate was filtered off, and the filtered solution was gently evaporated and then cooled, thus obtaining brown powder. A final product was obtained at a yield of 57% through recrystallization in methanol and drying in a vacuum oven at 60° C.

$^1$H-NMR (400 MHz, CD$_3$OD, δ): 8.82 (d, 1H, J=9.2, C$_5$H$_2$N), 8.43 (d, 1H, J=9.2 Hz, C$_6$H$_4$), 8.39 (d, 1H, J=8.8 Hz, C$_5$H$_2$N), 8.24 (d, 1H, J=8.2 Hz, C$_6$B$_4$), 8.15 (m, 1H, C$_6$B$_4$), 8.06 (d, 1H, J=15.6 Hz, CH), 7.90 (t, 1H, J=7.4 Hz, C$_6$H$_4$), 7.67 (d, 1H, J=16.0 Hz, CH), 7.52 (s, 1H, C$_6$H$_3$), 7.39 (dd, 1H, C$_6$H$_3$), 6.91 (d, 1H, J=8.0 Hz, C$_6$B$_3$), 6.83 (s, 2H, C$_6$H$_2$SO$_3^-$), 4.56 (s, 3H, NCH$_3$), 3.98 (s, 3H, OCH$_3$), 2.60 (s, 6H, 2CH$_3$), 2.21 (s, 3H, CH$_3$).

Comparative Example

The ZnTe crystal having a gloss surface and a thickness of 1.0 mm very widely useful as an inorganic THz generation material, and the organic OH1 crystal having a thickness of 0.37 mm as the recent electro-optic crystal for THz wave generation were used.

Because of comparatively high optical quality of the crystals having flat surfaces, the as-grown OH1 crystal was used without gloss treatment.

Experimental Example 1

THz Generation and Detection

Figure 9:
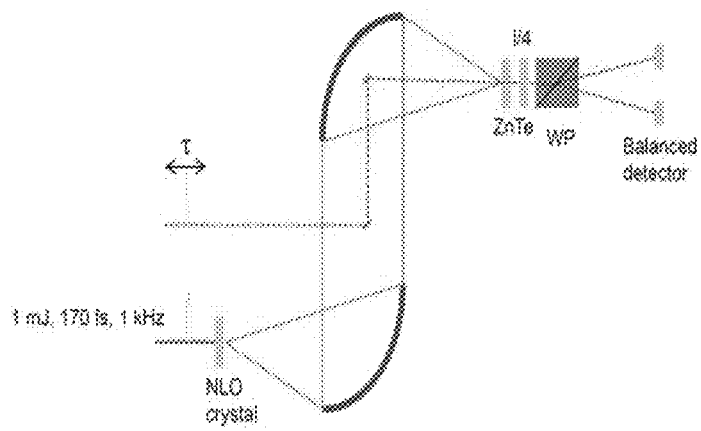
FIG. 9 illustrates the experimental setup for THz wave generation and detection.
Figure 10:
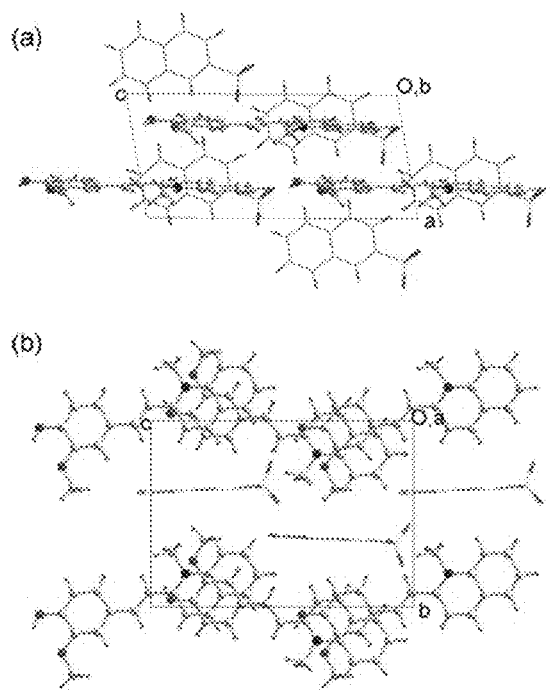
FIG. 10 illustrates results of X-ray structural analysis of the nonlinear optical crystal of Example 3.

The experimental setup for THz wave generation and detection is schematically illustrated in FIG. 9.

THz wave generation in nonlinear optical crystals by way of optical rectification (OR) is recorded using an electro-optic sampling (EOS) method using femtosecond laser pulses transferred from a regenerative amplified Ti:sapphire laser (Coherent Inc., Legend).

Optical pulses have a duration of 170 fs at 836 nm at a repetition rate of 1 kHz. The TM polarized (p-polarized) optical pulses were split by a 9:1 beam splitter as an optical pump and an electro-optic sampling probe. As such, in order to avoid damage to the sample, the pump beam was not focused. Because the diameter of the non-focused beam is 2 mm, the same beam spot size was made on the nonlinear optical crystal phase using a square iris of 1 mm×1 mm. The optical pump pulses were incident on the crystal phase through TM polarization just behind the iris.

The as-grown nonlinear optical crystal was placed on the rotating stage in order to optimize phase matching conditions.

The generated THz wave was collimated and focused on the ZnTe crystal phase with a 90° off-axis parabolic mirror pair.

The residual optical beam after THz generation was filtered under the condition that an Si wafer 350 μm thick was inserted. The focused THz beam was characterized using the cut 1 mm ZnTe crystal by way of EOS.

The amplitude of the THz field is represented by $$E_{THz} = \frac{\delta I}{\Delta I} \frac{2\lambda}{\pi l n^2 r_{41}},$$

wherein $E_{THz}$ is the amplitude of the generated THz wave, $\delta I$ is the photodiode intensity modulation due to the THz field in the ZnTe crystal, $\Delta I$ is the maximum intensity difference between balanced photodiodes, l is the thickness (1 mm) of the ZnTe crystal, $r_{41}$ is the electro-optic coefficient ($r_{41}$=4.1 pm/V) of ZnTe, and n is the refractive index (n=2.85) of ZnTe.

Figure 8:
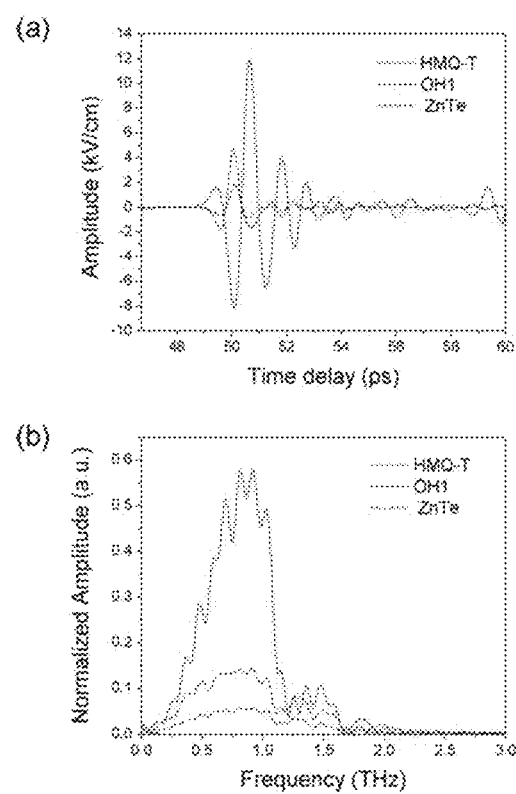
FIG. 8 illustrates the time-trace of THz waves generated from the nonlinear optical crystals of Examples 1 and 2 and Comparative Example.

In FIG. 8, (a) shows the time-trace of the THz waves generated from the nonlinear optical crystals in Examples 1 and 2 and Comparative Example.

The spectrum of the generated THz field is shown in (b) of FIG. 8, which is obtained by fast Fourier transform (FFT) of the THz time-trace of (a) of FIG. 8.

The THz wave generation efficiencies of HMQ-T crystals of Examples 1 and 2 are respectively 8.4 times and 3.1 times greater than the ZnTe and OH1 crystals in Comparative Example: the peak-to-peak amplitude of the THz field is 20.2 kV/cm in HMQ-T in the example, and is 2.4 kV/cm in ZnTe and is 6.5 kV/cm in the OH1 crystal in the comparative example.

Experimental Example 2

THz Generation and Detection (800 nm)

Figure 14:
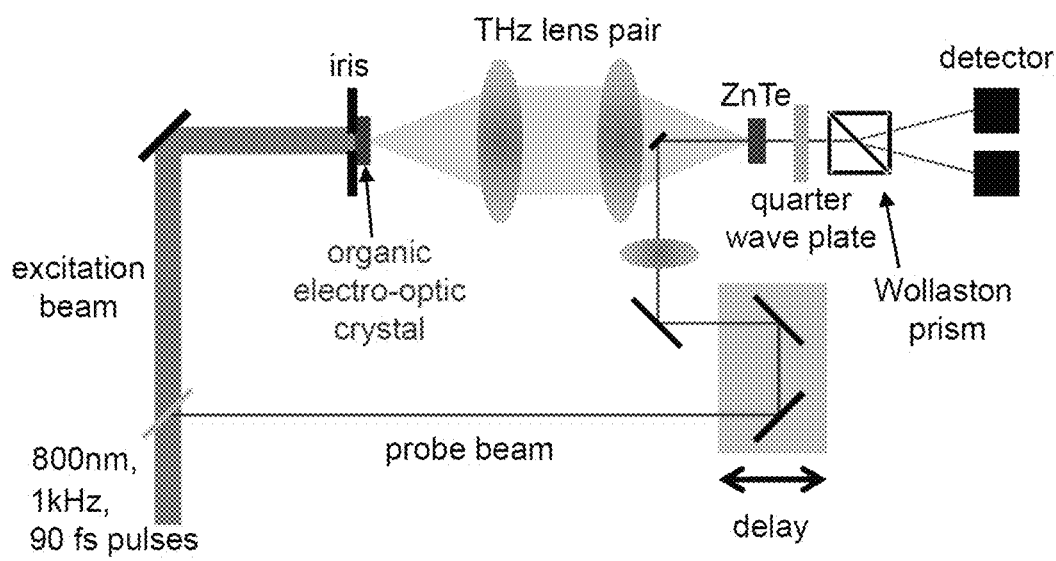
FIG. 14 illustrates the experimental setup (800 nm) for THz wave generation and detection.

The experimental setup for THz wave generation and detection is schematically illustrated in FIG. 14.

A Ti:sapphire regenerative amplifier system (Spitfire Ace, Spectra Physics) of 90-fs pulses at a repetition rate of 1 KHz at a wavelength of 800 nm was used. As illustrated in FIG. 14, the THz wave is generated by the OR method using femtosecond laser pulses, and is detected by the EOS method. To evaluate the efficiency of a variety of nonlinear crystals, an iris was located in front of the crystal. The frequency conversion efficiency of the nonlinear organic crystals is quite sensitive to its orientation, propagation direction and tilting angle. So, the sample mounting stage has to possess several degrees of freedom. The THz wave is propagated through a THz lens pair, focused on the 1 mm thick ZnTe crystal, and detected by an EOS detector. The probe beam causes THz wave-induced birefringence in the electro-optic crystal and is separated by way of a quarter wave plate and a Wollaston prism. Finally, the amplitude modulation of IR beam intensity is detected by means of two Si detectors and a lock-in amplifier having a chopping frequency of 150 Hz.

The present inventors recorded the THz time-trace while moving the stage powered after having been inserted into the excitation beam. Also, the intensity of the electric field of the THz wave may be calculated using the numerical relation between intensity modulation of the ZnTe crystal and the electro-optic coefficient.

Figure 15:
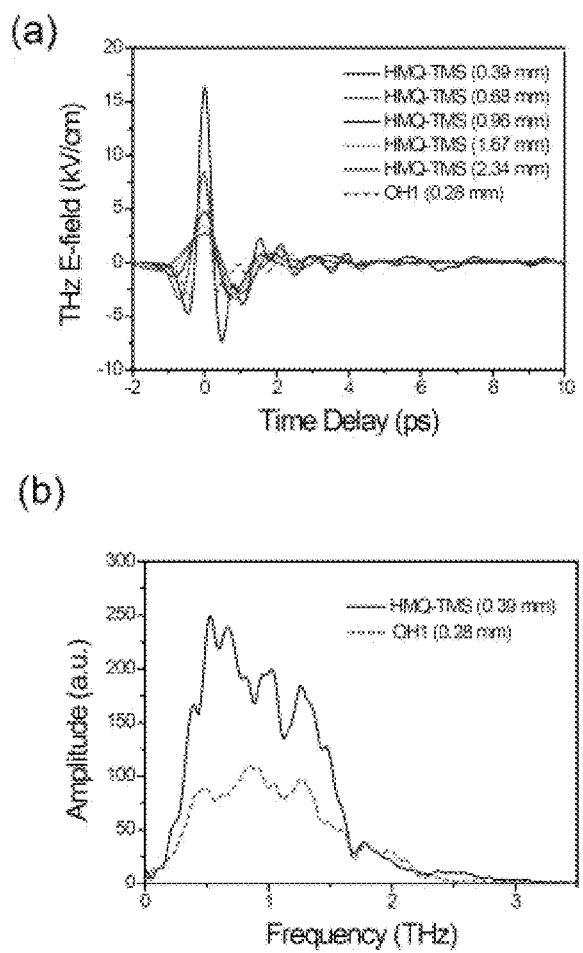
FIG. 15 illustrates the time-trace of THz waves generated from the nonlinear optical crystals of Example 4 and Comparative Example.

In FIG. 15, (a) shows the time-trace of THz waves generated from the nonlinear optical crystals of Example 4 and Comparative Example.

The spectrum of the generated THz field is shown in (b) of FIG. 15, which is obtained by way of fast Fourier transform (FFT) of THz time-trace of (a) of FIG. 15.

The THz wave generation efficiency of the HMQ-TMS crystal of Example 4 is greater than that of the OH1 crystal in Comparative Example, and HMQ-TMS in the example is much greater in peak-to-peak amplitude of the THz field than the OH1 crystal in the comparative example.

Even though phase matching and thickness conditions are not optimized, the quinolinium crystals according to the embodiments of the present invention are vastly superior in terms of high-power THz generation and applications thereof, compared to the comparative crystals.

Although the preferred embodiments of the present invention have been disclosed for illustrative purposes, those skilled in the art will appreciate that various modifications, additions and substitutions are possible, without departing from the scope and spirit of the invention as disclosed in the accompanying claims. The disclosed embodiments should be taken into consideration not from limited point of view but from descriptive point of view. The scope of the present invention is shown not in the above description but in the claims, and all differences within the range equivalent thereto will be understood to be incorporated in the present invention.

INDUSTRIAL APPLICABILITY

According to an embodiment of the present invention, quinolinium crystals can be applied to high-power THz generation and are thus industrially useful.

The invention claimed is:

1. A quinolinium derivative for use in nonlinear optics so as for a terahertz (THz) wave generation source (light source), as represented by Chemical Formula 1 or 2 below:

Chemical Formula 1

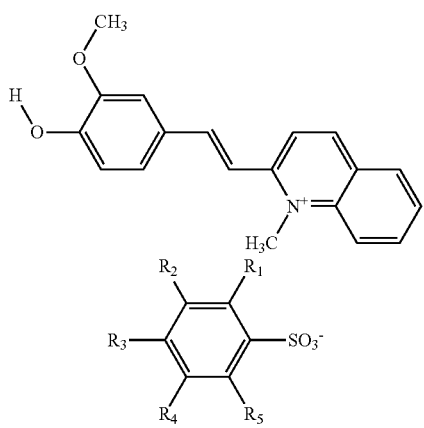

Chemical Formula 2

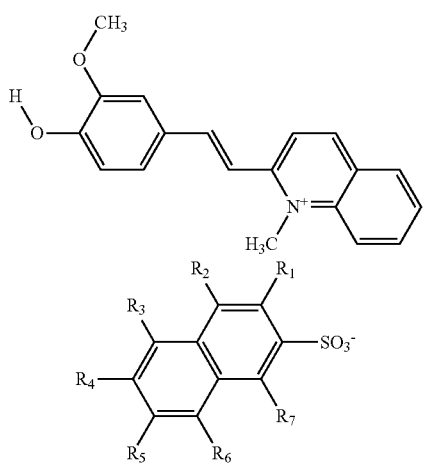

in Chemical Formulas 1 and 2, $R_1$~$R_7$ are each independently any one or more selected from among hydrogen, hydroxyl, halogen, pseudohalogen, formyl, carboxyl, alkyl, long-chain alkyl, alkoxy, long-chain alkoxy, cycloalkyl, haloalkyl, aryl, arylene, haloaryl, heteroaryl, heteroarylene, heterocycloalkylene, heterocycloalkyl, haloheteroaryl, alkenyl, haloalkenyl, alkynyl, haloalkynyl, keto, ketoaryl, haloketoaryl, ketoheteroaryl, ketoalkyl, haloketoalkyl, ketoalkenyl, haloketoalkenyl, phosphoalkyl, phosphonate, phosphate, phosphine, phosphine oxide, phosphoryl, phosphoaryl, sulfonyl, sulfoalkyl, sulfoarenyl, sulfonate, sulfate, sulfone, amine, polyether, silylalkyl and silylalkyloxy.

2. The quinolinium derivative of claim 1, wherein the quinolinium derivative is selected from among 2-(4-hydroxy-3-methoxystyryl)-1-methylquinolinium 4-methylbenzenesulfonate (HMQ-T), 2-(4-hydroxy-3-methoxystyryl)-1-methylquinolinium 4-methoxylbenzenesulfonate (HMQ-MBS), 2-(4-hydroxy-3-methoxystyryl)-1-methylquinolinium naphthalenesulfonate (HMQ-NS), 2-(4-hydroxy-3-methoxystyryl)-1-methylquinolinium 2,4,6-trimethylbenzenesulfonate (HMQ-TMS), and 2-(4-hydroxy-3-methoxystyryl)-1-methylquinolinium 6-hydroxy naphthalenesulfonate (HMQ-HNS).

3. An optical rectification (OR) or difference frequency generation (DFG) method using a crystal comprising the quinolinium derivative represented by claim 1 and Chemical Formula 1 or 2.

4. A teraherz wave generated using the optical rectification (OR) or difference frequency generation (DFG) method of claim 3.

* * * * *